United States Patent [19]

Cole et al.

[11] Patent Number: 5,141,850

[45] Date of Patent: Aug. 25, 1992

[54] POROUS STRIP FORM ASSAY DEVICE METHOD

[75] Inventors: Francis X. Cole, Stow; Eric C. Sigillo, Methuen; Paul C. MacDonnell, Bedford; Nancy J. Cicia, Wakefield, all of Mass.

[73] Assignee: Hygeia Sciences, Inc., Newton, Mass.

[21] Appl. No.: 475,486

[22] Filed: Feb. 7, 1990

[51] Int. Cl.$^5$ ............................................. G01N 33/53
[52] U.S. Cl. ................... 436/525; 435/7.92; 435/7.94; 435/969; 435/970; 435/971; 435/7.5; 436/535; 436/540; 436/541; 436/810; 436/818; 422/56; 422/58
[58] Field of Search ............... 435/7.5, 7.92, 7.94, 435/969, 970, 971; 436/525, 535, 538, 540–541, 810, 818; 422/56, 58

[56] References Cited

U.S. PATENT DOCUMENTS

| | | | |
|---|---|---|---|
| 4,094,647 | 6/1978 | Deutsch et al. | 436/810 X |
| 4,313,734 | 2/1982 | Leuvering | 436/818 X |
| 4,366,241 | 12/1982 | Tom et al. | 435/7.91 |
| 4,373,932 | 2/1983 | Gribnau et al. | 436/538 X |
| 4,496,654 | 1/1985 | Katz et al. | 436/818 X |
| 4,552,839 | 11/1985 | Gould et al. | 436/541 X |
| 4,772,550 | 9/1988 | Greenquist | 436/810 X |
| 4,774,192 | 9/1988 | Terminiello et al. | 436/518 X |
| 4,778,751 | 10/1988 | El Shami et al. | 436/541 X |
| 4,803,170 | 2/1989 | Stanton et al. | 436/518 |
| 4,806,311 | 2/1989 | Greenquist | 435/7.4 X |
| 4,853,335 | 8/1989 | Olsen et al. | 436/525 X |
| 4,859,612 | 8/1989 | Cole et al. | 436/525 X |
| 4,861,711 | 8/1989 | Friesen et al. | 436/810 X |
| 4,868,108 | 9/1989 | Bahar et al. | 435/7.92 |
| 4,891,313 | 1/1990 | Berger et al. | 435/969 X |
| 4,945,042 | 7/1990 | Geiger et al. | 435/7.5 |
| 4,963,468 | 10/1990 | Olson | 435/7.94 |

FOREIGN PATENT DOCUMENTS

| | | | |
|---|---|---|---|
| 0201079 | 11/1986 | European Pat. Off. | 435/7.5 |
| 0337082 | 10/1989 | European Pat. Off. | 435/7.5 |

*Primary Examiner*—Esther L. Kepplinger
*Assistant Examiner*—Carol A. Spiegel
*Attorney, Agent, or Firm*—Staas & Halsey

[57] ABSTRACT

An immunoassay method comprising applying an aqueous solution containing the analyte antigen to one end of a multi-zoned test strip device such that the solution moves along the strip by capillary action. The zones are arranged so that the solution (a) first contacts and reconstitutes dry, diffusible labelled component comprising colloidal gold conjugated to an antibody specific for said analyte antigen and then (b) contacts and reconstitutes dry, diffusible biotinylated second antibody specific for said analyte antigen such that a diffusible, dispersed sandwich reaction product forms. The reaction product diffuses along the strip with the solution and into a zone containing capture component consisting of a latex and avidin complex which avidin collects the reaction product by means of reaction with its biotin moiety. Thus, gold particles are collected and concentrated in the detection zone for visual determination.

52 Claims, 1 Drawing Sheet

POROUS STRIP FORM ASSAY DEVICE METHOD

BACKGROUND OF THE INVENTION

1. Field of the Invention

The present invention relates to immunoassays for determining and detecting the presence of immunologically reactive analytes in aqueous samples and in particular to self contained, single step, solid phase strip form assay devices and methodology.

2. Prior Activities and the State of the Art

Assays based on reactions between specifically immunoreactive substances are used extensively today in fields such as clinical medicine, forensic medicine, environmental testing, food quality assurance, drug testing and other related areas for detecting the presence of immunoreactive analytes in test samples.

The development of non-radioactive labels or markers has facilitated the use of immunoassay diagnostic procedures outside of laboratory settings and in remote sites such as physician's offices and even the homes of the users. In the physician's office, immunological procedures are useful for providing rapid, simple assays which may be performed while the patient is still in the office so that the diagnosis can be accomplished without delay and treatment instituted during a single visit. Without such simple assays, it was often necessary for the physician to collect a sample from a patient during a first visit and to have the sample analyzed by a clinical laboratory with the results reported back to the physician by the laboratory at a later time. In the meanwhile, the patient was sent home and was required to return for a second visit with the physician in order to receive appropriate treatment and/or medication. Manifestly, such delay was inefficient and inappropriate and in some cases even be life threatening.

Home testing has become desirable to facilitate testing by the consumer in the privacy of his or her own home. The results of such testing might, for example, indicate the necessity or lack of necessity of a visit to the physician. Examples of useful tests for the "at home" market include tests for pregnancy, ovulation, streptococcus infection and other infections which ar detectable by analysis of body fluids such as urine, saliva, throat fluids, pus, vaginal fluids, blood or other appropriate test samples.

For remote site testing, assuming appropriate sensitivity and specificity can be achieved, there are at least three other requirements for practical assay procedures. The first of these desirable factors is speed in that the assay must be performed in an acceptably short period of time, the shorter the better. Stability is also a desirable feature in that the components of the assay should be stable for an extended period of time without refrigeration or special handling. Finally, from a commercial view point it is desirable that the test be convenient to use and as simple as possible requiring only minimal or n instrumentation and precluding mistakes and poor performance resulting in incorrect interpretations.

One of the difficulties encountered in the development of test devices for remote site testing is the provision of a practical pre-packaged disposable device to facilitate efficient, relatively inexpensive, fool proof test procedures. This, of course, requires a device which is inexpensive to construct, which has a shelf life appropriate to the commercial use of the device, which is protected against contamination during handling, which may be simply and conveniently utilized when the appropriate time arises, and which may conveniently and safely be used by even untrained persons.

The device illustrated in U.S. Pat. No. 4,868,108 addresses some of these problems; however, this device incorporates a test which utilizes enzyme color formers that depend on the presence of substrates and are often unstable and adversely influence shelf life. The '108 patent is commonly assigned and the entirety of the disclosure thereof is hereby specifically incorporated by reference.

Another known device is disclosed in U.K. Patent Application G.B. 2204398A. This device uses colloidal gold or colored particles as so called "direct" labels; however, in this device the non-labelled reaction component is permanently immobilized at the observation zone. This effects the efficiency of the analyte detection mechanism.

These prior devices leave unsatisfied the need for a simple inexpensive, efficient, fool proof, pre-packaged, one step device that has good shelf life characteristics.

SUMMARY OF THE INVENTION

The present invention provides a simplified, inexpensive, efficient, fool-proof, pre-packaged, one step device that has good shelf life characteristics. Moreover, in accordance with the present invention the detection reactions occur in a liquid phase with all components in a freely mobile state. This improves the efficiency and rapidity of the invention. In further accordance with the present invention, a process is provided for the determination and detection of an immunologically reactive analyte in an aqueous sample. In one aspect of the invention the process includes the steps of providing a water-dispersible labelled component that comprises the coupling product of a first immunologically reactive substance and a detectable species; providing a water-dispersible capturable component that comprises the coupling product of a capturable species and a second immunologically reactive substance; providing a capture component that is localized at a detection zone in a porous carrier material and which comprises a capturing substance capable of interaction with a reaction product containing the capturable species to thereby capture and collect the product at the detection zone; contacting the labelled and capturable components with an aqueous solution comprising a sample to be analyzed for the analyte to thereby form a liquid reaction mixture containing said sample and said components, said first and second substances being the same or different and capable of binding directly or indirectly as a function of the presence of said analyte to thereby form a dispersed, diffusible reaction product containing the capturable product component; causing the liquid reaction mixture to contact the capture component at the detection zone whereby reaction product containing said capturable component is collected at said zone by interaction with the capturing substance; and determining or detecting the analyte in the sample by evaluating the presence of detectable species in the reaction product immobilized at the zone.

In accordance with a particularly preferred aspect of the invention, the labelled component and the capturable component may each initially be dry, reconstitutible, water-dispersible and diffusible. And in accordance with this aspect of the invention the components are reconstituted when the same are contacted by an aqueous solution which comprises the sample to be analyzed for the analyte.

In accordance with another particularly preferred aspect of the invention, the labelled component and the capturable component are each contained in a porous carrier material and the liquid reaction mixture is caused to diffuse and migrate through the porous carrier material to bring reaction product into contact with the capture component at the detection zone.

In yet another aspect of the invention, the labelled component and the capturable component are each contained in a zone in a porous carrier material and the liquid reaction mixture is caused to diffuse and migrate through the porous carrier material and into the detection zone to bring reaction product into contact with the capture component at the detection zone.

And in yet further aspect of the invention, the labelled component is contained at a first zone in an elongated strip of porous carrier material and the capturable component is contained at a second zone in the strip of porous carrier material. The detection zone is also in the strip of porous carrier material. In a preferred aspect of the invention the first and second zones may be spaced apart longitudinally of the strip. Additionally, the detection zone may be longitudinally spaced from one end of the strip and the first and second zones may be disposed between the end of the strip and the detection zone. In accordance with the particularly preferred form of the invention the step of causing the mixture to come into contact with the capture component may be accomplished by diffusion and migration of the mixture along the strip from said first and second zones to the detection zone. Moreover, the step of reconstituting the components may include the step of applying the liquid sample to said one end of the strip whereby the sample diffuses along the strip and into the first and second zones.

The invention also provides a device for conducting a process for the determination and detection of an immunologically reactive analyte in an aqueous sample. The device of the invention comprises a water-dispersible labelled component that comprises the coupling product of a first immunologically reactive substance and a detectable species. The device also includes a water-dispersible, capturable component that comprises the coupling product of a capturable species and a second immunologically reactive substance. The first and second substances may be the same or different and capable of binding directly or indirectly as a function of the presence of said analyte to thereby form a water-dispersible, diffusible reaction product containing the capturable component. The device also includes a capture component localized at a detection zone in a porous carrier material and the capture component may comprise a capturing substance capable of interaction with reaction product containing the capturable species to thereby capture and collect the product at the detection zone.

In a preferred form of the invention the device may comprise an elongated strip of porous carrier material. In this form of the invention the labelled component is contained at a first zone in the strip of porous carrier material and the capturable component is contained at a second zone in the strip of porous carrier material. The detection zone is also located in the strip of porous carrier material. In this form of the invention, the first and second zones may be spaced apart longitudinally of the strip and the detection zone may be longitudinally spaced from one end of the strip with the first and second zones disposed between the end of the strip and the detection zone in longitudinally spaced relationship relative to the latter. Ideally the device may include a wick member in intimate contact with the element at said one end thereof.

DETAILED DESCRIPTION OF THE PREFERRED EMBODIMENTS OF THE INVENTION

Figure 1:
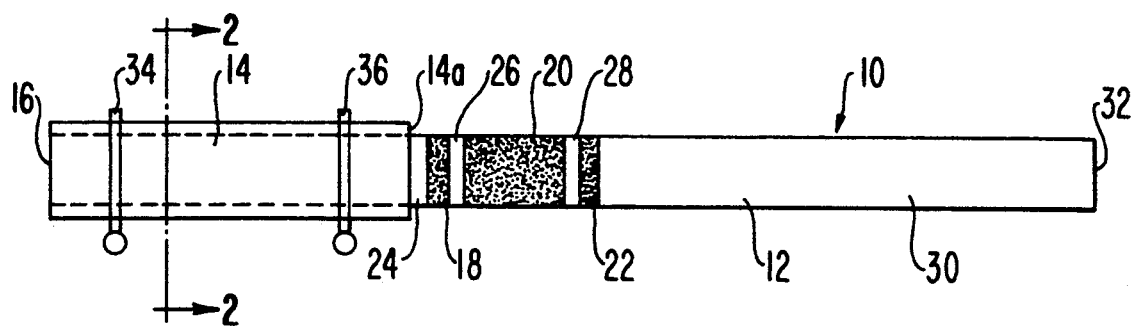
FIG. 1 is a schematic representation of an assay device in accordance with the invention.

A device 10 for the determination and detection of an immunologically reactive analyte in a liquid sample and which embodies the principles and concepts of the invention is illustrated in FIG. 1. The device 10 includes a base element 12 of a porous, preferably microporous, carrier material. As illustrated in FIG. 1 the base element 12 is in the form of an elongated strip of the porous carrier material. Preferably, the porous carrier material from which the strip 12 is formed should have a pore size less than about $25\mu$ and typically the pore size may be between about 5 and about $10\mu$. Strip 12 may be formed of a bibulous material, for example, nylon or a cellulosic material. A particularly useful material, in accordance with the invention, is a commercially available material known as Ahlstrom No. 345 paper. This material is smooth and white and is composed of 100% cellulose. The preferred material has a basis weight of about 158 g/m$^2$, a thickness of about 0.7 mm and capillary rise characteristics, relative to an aqueous solution, of about 80 mm/min. Of course, different types of materials may be utilized depending on the desired characteristics of a particularized assay procedure. For example, commercially available materials known as Whatman 903 and Whatman 31ET papers have been found to be useful in accordance with the invention.

Figure 2:
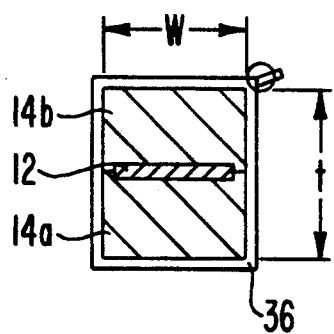
FIG. 2 is an enlarged cross-sectional view taken along the line 2—2 of FIG. 1.

A wick member 14 is attached to strip 12 at one end 16 thereof, as can be seen in FIGS. 1 and 2. Wick 14 may preferably be formed from a bonded cellulose acetate fibrous material that is available commercially from American Filtrona either in a form where the fibers are aligned or in a non-aligned (biaxially arranged) form. The wick member 14 may be formed from an elongated block of material that is split into separate rectangular pieces 14a and 14b which are then pressed tightly against respective opposite surfaces of element 12 so that wick member 14 and strip 12 are in intimate, capillary communicating contact. For this purpose the separate pieces 14a and 14b may be held tightly together and against the surfaces of strip 12 using a pair of bands 34 and 36. These bands 34 and 36 may be devices known commercially as BAR-LOK cable ties (Dennison Part No. 08429; Military Std. 3367-4-9).

With reference to FIGS. 1 and 2, it should be pointed out that the various dimensions are not necessarily drawn to scale. In a useful form of the invention strip 12 may have a length, for example, of approximately 150 mm, and a width, for example, of approximately 9.5 mm. The thickness of strip 12 may range from 0.5 to 1.0 mm and preferably may be about 0.7 mm. However, the specific dimensions of the strip are not critical and the various dimensions may be modified as necessary to achieve desired results of speed and/or color intensity to reveal a positive test result.

The wick member 14 may initially be about 51 mm in length, about 10.5 mm in width (w) and about 12.5 mm in thickness (t). And the elongated wick 14 is preferably positioned so as to extend along the length of element 12, as shown in FIG. 1.

The device 10 includes a series of zones 18, 20 and 22 located in strip 12. Zone 20 contains a dry, reconstitutible, water-dispersible, diffusible labelled component which comprises a first immunologically reactive substance. The labelled component in zone 20 preferably comprises the coupling product of the first immunologically reactive substance and a detectable species. Zone 18 contains a dry, reconstitutible, water-dispersible, diffusible capturable component which comprises a second immunologically reactive substance. A capture component is localized at detection zone 22 and comprises a capturing substance capable of interaction with the capturable component to capture and collect the capturable component at the detection zone. Thus, the capturing substance is capable also of capturing and collecting the capturable component and anything that is bound thereto.

In the useful form of the invention illustrated in FIGS. 1 and 2, zones 18 and 20 are spaced apart longitudinally of strip 12. However, it should be appreciated that these zones might be superimposed. Moreover, the relative positions of zones 18 and 20 might as well be reversed. With reference to FIG. 1 it also can be seen that detection zone 22 is spaced longitudinally from end 16 of strip 12 and that zones 18 and 20 ar disposed between end 16 and zone 22 in longitudinally spaced relationship relative to the latter.

Wick member 14 is disposed to extend along element 12 from end 16 and toward zones 18 and 20. Preferably wick 14 terminates in spaced relationship relative to zone 18 as shown, with the end 14a of wick 14 disposed approximately 2.5 mm from zone 18 so as to present a space 24 therebetween. Additionally, a space 26 is presented between zones 18 and 20 and a space 28 is presented between zones 20 and 22. Finally, a space 30 extends from zone 22 to the end 32 of strip 12. Measured along the length of element 12, wick 14 has a preferred dimension of about 51 mm, space 24 has a preferred dimension of about 2.5 mm, zone 18 has a preferred dimension of about 20 mm, space 26 has a preferred dimension of about 2.5 mm, zone 20 has a preferred dimension of about 14 mm, space 28 has a preferred dimension of about 2.5 mm, zone 22 has a preferred dimension of about 2.6 mm and space 30 has a preferred dimension of about 71.9 mm.

The immunologically reactive substance of the labelled component in zone 20 and the immunologically reactive substance of the capturable component contained at zone 18 may be the same or different, the only requirement of the invention being that the same must be capable of binding directly or indirectly as a function of the presence of a target immunologically reactive analyte in a liquid sample to thereby form a water-dispersible, diffusible reaction product which contains the capturable component and the labelled component.

In accordance with one preferred form of the invention the immunologically reactive substances may each be capable of binding the analyte to form a sandwich. In this regard, the substances may each be monoclonal antibodies capable of immunologically binding a target antigen analyte. Alternatively, suitably pure polyclonal antibodies of appropriate specificity could be employed. Preferably, such antibodies bind respective different sites on the antigen.

In another form of the invention, the immunologically reactive substances may bind each other, that is to say, one of the substances may be an antigen and the other may be an antibody thereto. The immunologically reactive substance of the labelled component may be an antigen, and in this form of the invention, the assay procedure may rely on a competitive inhibition procedure to detect an unknown antigen analyte in the sample.

As set forth above, the labelled component comprises the coupling product of an immunologically reactive substance and a detectable species. Preferably, the detectable species may be a metal-containing particle of the sort fully described in U.S. Pat. No. 4,859,612 which is incorporated herein by specific reference. Thus, gold sol particles having a particle size in the range from about 25 to about 1000 Å may be coated with antibody or antigen for use in accordance with the present invention. Such coated particles are intensely colored, either orange, red or violet depending on particle size.

However, the present invention does not depend on the specific nature or characteristics of the label or of the immunologically reactive substance and should be broadly useful in connection with any sort of label that may be coupled to an immunologically reactive substance.

The capturable component contained at zone 18 also comprises an immunologically reactive substance. In addition, the capturable component may include a capturable species whereby the capturable component comprises the coupling product of the capturable species and the immunologically reactive substance.

The capture component localized at detection zone 22 preferably comprises a capturing substance that is capable of interaction with the capturable component so that a reaction product containing the capturable component may be captured and collected at the detection zone. The capturing substance may be linked directly to the cellulose material from which the strip 12 is formed. In a preferred form of the invention, however, the capturing substance may be coupled to a solid phase particle which has a size and character such that the same may be deposited and thus localized in the pores of the porous carrier material at the detection zone. In this form of the invention, the solid phase particle may comprise any one of a number of known, water-dispersible particles, such as, for example, the various particles disclosed in the above-identified '612 patent. Solid phase particles useful in connection with the invention include, for example, particles of latex or other support materials such as silica, agarose, glass, polyacrylamides, polymethyl methacrylates, carboxylate modified latex and SEPHAROSE. Preferably, the particles will vary in size from about $0.2\mu$ to about $10\mu$. A particularly preferred material for use in connection with the present invention comprises the 0.99 micron ($\mu$) carboxylate modified latex particles (Polysciences) described in co-assigned and co-pending U.S. application, Ser. No. 177,114, filed Apr. 4, 1988, the entirety of the disclosure of which is also hereby specifically incorporated by reference.

In a specifically preferred form of the invention, the device 10 may be used to determine pregnancy. For this used purpose the human chorionic gonadotropin (hCG) specific 2B2 monoclonal antibody described in said '612 patent may be used. The 2B2 antibody may be coupled to biotin, the latter thus serving as a capturable species. To biotinylate the 2B2 antibody, 50 mg of biotin-e-aminocaproic acid N-hydroxysuccinimide ester (Biotin-X-NHS, Cal. Biochem.) is first dissolved in 5 ml of dimethyl sulfoxide (DMSO). A solution containing the antibody is prepared by admixing 13.32 ml of 1M $Na_2CO_3$ and 80 ml of 0.15M NaCl and then adding 833.35 mg or dialyzed 2B2 antibody and 29.3 ml of DMSO to the admixture. The initial solution of biotin and DMSO is then added to the antibody solution and the complete mixture is allowed to react for about 2 hours at room temperature. After incubation, the 2B2/biotin conjugate thus formed is dialyzed against a 0.15M NaCl/0.05% $NaN_3$ solution for 48 hours at 4° C. The conjugate is then added to an amount of a buffered solution (ph 8.0±0.05) containing 12.11 g/l Tris base, 100 g/l MALTRIN 365 (Grain Processing Corp.), 3 g/l EDTA disodium salt, 0.3 ml/l IGEPAL CA 720 (GAF Company), 0.1 g/l thimerosal such that the concentration of the protein is approximately 0.5 g/l. 2 µl of the resultant solution is spread on strip 12 at zone 18 and allowed to dry. The functionalities and compositional characteristics of the various components of the buffered solution are described fully in co-assigned, co-pending application Ser. No. 07/344,575, the entirety of the disclosure of which is hereby incorporated by specific reference.

In a preferred form of the invention, the labelled component in zone 20 ideally comprises the coupling product of a first immunologically reactive substance and a detectable species. For detection of pregnancy the preferred immunologically reactive substance is the hCG specific 2G9 monoclonal antibody described in said '612 patent and the preferred detectable species comprises the gold sol particles also described in the '612 patent. Antibody coated gold sol particles may be prepared essentially as set forth in the '612 patent and preferably the gold sol particles may have a diameter of approximately 30 nm. (See G. Frens, Nature. 241, 20-22 (1973)). The antibody coated gold sol particles may be processed as set forth in the '612 patent to produce a final product comprising gold labelled probe particles which may then be used as the labelled component in the preferred form of the invention. Such gold labelled probe particles comprise approximately 10.2 mg of the 2G9 antibody for each 1000 $OD_{533nm}$ units of 30 nm gold sol particles.

The antibody coated gold sol particles are incorporated in a solution containing 45.45 g/l bovine serum albumin (BSA), 0.667 g/l sodium azide, 9.09 ml per liter TRITON X-100, 8.69 g/l Tris base, 253.64 g/l MALTRIN 365, 0.215 ml IGEPAL CA 720, 0.0718 g/l thimerosal, and 8 mg/l of 2G9 antibody coated on 785.45 $OD_{533nm}$ units of the gold sol particles. 50 µl of this solution is then applied so as to cover zone 20 of device 12 and the solution is allowed to air dry. TRITON X-100 is an octylphenoxypolyethoxyethanol nonionic surfactant that is a commercial product of Rohm and Haas Company.

The capture component for zone 22 may comprise an avidin material, for example streptavidin, conjugated to solid latex particles. The streptavidin latex particles may then be deposited and thus localized within the pores of the porous carrier material of strip 12 at zone 22. To prepare streptavidin latex particles, 280 mg of streptavidin is dissolved in 560 ml of 0.15M NaCl. In a separate vessel 1050 ml of 0.30M NaCl is added to 800 ml of a latex suspension containing 15.47 g of 0.99µ carboxylate modified latex (Polysciences). A sufficient amount of purified water is added to bring the total volume of the latex containing suspension to approximately 2 liters. To activate the latex, 10.5 g carbodiimide in 105 ml of water is added to the latex suspension and the latter is allowed to react for about 10 minutes. The carbodiimide activated latex is then collected in a centrifuge and resuspended in approximately 1540 ml of 0.14M NaCl solution. The streptavidin solution prepared above is then mixed with the activated latex suspension and the mixture is stirred for 15 to 20 hours. After the reaction is complete, 210 ml of a 1M glycine solution is added to the streptavidin latex suspension and the suspension is again stirred for about an hour. The mixture is centrifuged and the supernatant aspirated. Thereafter the streptavidin latex conjugate is washed with a mild saline solution and again subjected to centrifugation. The product is resuspended in a sufficient amount of an aqueous solution containing 300 g/l MALTRIN 365 and 0.5 g/l sodium azide to produce a final suspension containing approximately 735 g of streptavidin latex per liter. 20 µl of such suspension, which contains approximately 1.47 mg of streptavidin latex, is then applied to zone 22. The suspension is applied to zone 22 while a vacuum (19 inches of water) is applied to the opposite side of strip 12 to prevent the streptavidin latex from spreading beyond the zone and to make sure that the latex particles completely impregnate the pores of strip 12 at zone 22.

Prior to the application of wick element 14 to strip 12, the wick preferably treated with a solution containing 12.1 g/l Tris base, 100 g/l MALTRIN 365, 3 g/l EDTA disodium salt, 0.3 ml per liter IGEPAL CA 720, 0.1 g/l thimerosal, 10 g/l BSA and 5 ml per liter of TRITON X-100. The treatment comprises immersing the wick 14 in the solution and allowing the solution to dry. Such treatment has been found to inhibit non-specific adsorption.

In use, the test solution simply needs to be applied to the end 16 of device 10. In the case of a pregnancy test, the wick 14 may be exposed to the liquid sample by being placed directly in a stream of first morning urine. If the test subject is pregnant such urine will contain human chorionic gonadotropin (hCG), a hormone analyte which is immunologically reactive, having a first site which is specifically immunoreactive with respect to the 2B2 antibody and another site which is specifically immunoreactive relative to the 2G9 antibody.

The urine is wicked up by the wicking action of wick member 14, and since the latter is in intimate contact with the surfaces of element 12, the pores of element 12 will cause the urine to migrate along strip element 12 by capillary action in a direction from end 16 and toward end 32. As the urine successively traverses zones 18 and 20 due to the capillary action of the pores of element 12, the urine will come into contact with the dry labelled and capturable components to reconstitute these components and thus form a liquid reaction mixture containing the urine and the components dispersed therein.

Since the 2B2 antibody of the capturable component from zone 18 is immunoreactive relative to a specific site on the hCG molecule, and since the 2G9 antibody of the labelled component from zone 20 is immunoreactive relative to a different specific site on the hCG molecule, a reaction product will be formed comprising a sandwich of the labelled 2G9 component, the hCG and the biotinylated 2B2 component.

Significantly the reactions which result in the formation of the reaction product take place in a liquid system wherein the reactants are all freely mobile. Thus, the reaction is efficient and provides positive results with minimal amounts of reactants and at low levels of analyte.

The urine with the reaction product dispersed therein will continue to diffuse and migrate along strip 12 by capillary action until the admixture encounters the streptavidin that is coupled to the latex particles localized at zone 22. Reaction between the streptavidin coupled to the latex particles and the biotin coupled to the 2B2 antibody in the reaction product, which also includes the gold sol label coupled to the 2G9 antibody, results in the capture and collection of the reaction product at zone 22. Thus, the localized capture component at zone 22 comprises the avidin as a capturing species which is capable of binding interaction with a reaction product containing a capturable component comprising biotin as a capturable species. The avidin interacts with the biotin to capture and collect the reaction product at zone 22 Which thus becomes a zone where the gold label is concentrated and detectable visually. The gold is collected and concentrated at zone 22 to produce a readily visible coloration which can be detected visually to indicate a positive result.

If the urine sample does not contain hCG the gold labelled 2G9 antibody will simply diffuse through zone 22 to be spread along space 30 where the individual gold particles will be so diffuse that the distinctive coloration thereof cannot be seen. Although the biotinylated 2B2 antibody will always be collected and concentrated at zone 22, there is no way to collect the gold labelled 2G9 antibody at that location in the absence of hCG.

In the foregoing specific examples, streptavidin has been employed as the capturing substance and biotin has been employed as the capturable species. These materials have been chosen because they interact quickly and firmly to provide a positive capture and collection function. Other avidin materials may be used as well. Moreover, the invention is not restricted to these specific materials and other alternative interacting materials could be employed. For example, antibodies may be raised against fluorescein thiocyanate, and the binding interaction between such antibodies and the fluorescein thiocyanate could be used to capture and collect the reaction product. Thus, 2B2 antibody may be coupled to the fluorescein thiocyanate to present the capturable component, and the antibody to fluorescein thiocyanate could be coupled to solid phase particles to present the localizable capture component. Other potential materials are known in the art, the only restriction in this regard being that the capturable species must be bindable to an appropriate immunologically reactive substance to thereby present the capturable component, and the capturing substance must be capable of being localized in an appropriate detection zone.

We claim:

1. An immunoassay of an aqueous sample for determining an immunoreactive analyte, said process comprising the steps of:
    providing an immunoassay device which comprises (1) an element being formed from a bibulous carrier material having a porous structure through which an aqueous dispersion system is capable of diffusing by capillary action, and (2) a capture component localized at a detection zone in the strip element, said capture component comprising a capturing species capable of specifically binding to a capturable species, said detection zone being spaced from at least one of the ends of the strip element;
    forming an aqueous dispersion system containing (a) the aqueous sample to be assayed for said analyte, (b) a first batch of dispersed first particles comprising a first coupling product of a first immunoreactive substance and a detectable label, and (c) a second batch of dispersed second particles comprising a second coupling product of a second immunoreactive substance and the capturable species, said first and said second immunoreactive substances being the same or different and being capable of specifically binding either competitively or non-competitively to said analyte or to one another as a function of the presence or quantity of said analyte in said system to thereby form a dispersed composite reaction product comprising both first and second particles;
    causing said aqueous dispersion system to diffuse along said strip element and through the bibulous material thereof and into said detection zone so as to bring the composite reaction product into contact with said capture component to thereby immobilize and concentrate the composite reaction product at the detection zone; and
    evaluating the detection zone for the presence of the detectable label as an indicator of the presence or quantity of the immunoreactive analyte in the aqueous sample.

2. The process as set forth in claim 1, wherein the first and second particles are initially both contained in said bibulous carrier material in a dry, reconstitutable, water-dispersible form, and wherein said aqueous dispersion system is formed by contacting the dry, reconstitutable particles with said aqueous sample.

3. The process as set forth in claim 2, wherein the contact between the aqueous sample and the dry, reconstitutable particles is caused to occur by first brining the strip element into contact with the aqueous sample and then allowing the sample to diffuse through the bibulous carrier material and into contact with the dry, reconstitutable particles.

4. The process as set forth in claim 3, wherein said dry, reconstitutable, water-dispersible particles are initially contained in one or more contact zones in said bibulous carrier material, and said aqueous dispersion system is formed by diffusion of said aqueous sample through said contact zones.

5. The process as set forth in claim 4, wherein said first batch of particles is contained in a first contact zone in said bibulous material and said second batch of particles is contained in a second contact zone in said bibulous material.

6. The process as set forth in claim 5, wherein said step of bringing the strip element into contact with the aqueous sample comprises immersing said one end of the base element in the aqueous sample.

7. The process as set forth in claim 1, wherein said detectable label comprises a metal-containing third particle.

8. The process as set forth in claim 7, wherein said first coupling product is prepared by coupling the first immunoreactive substance directly to the metal-containing third particle.

9. The process as set forth in claim 7, wherein said metal containing third particles are metal sol particles.

10. The process as set forth in claim 9, wherein said metal sol particles have a particle size in the range of from about 25 to about 1000 Angstroms.

11. The process as set forth in claim 9, wherein said metal sol particles are gold sol particles.

12. The process as set forth in claim 1, wherein one of said capturing and capturable species comprises biotin and the other species comprises avidin.

13. The process as set forth in claim 12, wherein said capturable species comprises biotin and said capturing species comprises avidin.

14. The process as set forth in claim 1, wherein said capture component comprises a third coupling product of a fourth particle and said capturing species, said fourth particle being deposited and thus immobilized in the pores of the immobilized carrier material at said detection zone.

15. The process as set forth in claim 14, wherein said capturable species comprises biotin and said capturing species comprises avidin.

16. The process as set forth in claim 5, wherein said first and second contact zones are spaced apart longitudinally of said strip element.

17. The process as set forth in claim 5, wherein said first and second contact zones are disposed between said one end of the strip element and said detection zone in longitudinally spaced relationship relative to the detection zone.

18. The process as set forth in claim 5, wherein said detectable label comprises a metal-containing third particle.

19. The process as set forth in claim 18, wherein said first coupling product is prepared by coupling the first immunoreactive substance directly to the metal-containing third particle.

20. The process as set forth in claim 18, wherein said metal containing third particles are metal sol particles.

21. The process as set forth in claim 20, wherein said metal sol particles have a particle size in the range of from about 25 to about 1000 Angstroms.

22. The process as set forth in claim 20, wherein said metal sol particles are gold sol particles.

23. The process as set forth in claim 5, wherein said capture component comprises a third coupling product of a fourth particle and said capturing species, said fourth particle being deposited and thus immobilized in the pores of said bibulous carrier material at said detection zone.

24. The process as set forth in claim 23, wherein said capturable species comprises biotin and said capturing species comprises avidin.

25. The process as set forth in claim 5, wherein said first and second immunoreactive substances each specifically binds a respective different site of the analyte to form a sandwich.

26. The process as set forth in claim 25, wherein said first and second immunoreactive substances are each antibodies and the analyte is an antigen which is specifically bound by both antibodies.

27. The process as set forth in claim 5, wherein said first and second immunoreactive substances specifically bind each other.

28. The process as set forth in claim 27, wherein one of said immunoreactive substances is an antibody and the other is an antigen which is specifically bound by said antibody.

29. The process as set forth in claim 27, wherein the first immunoreactive substance is an antibody and the second immunoreactive substance is an antigen which is specifically bound by said antibody.

30. A kit of materials for immunoassay of an aqueous sample for determining an immunoreactive analyte, said kit comprising:

an immunoassay device which comprises (1) an elongated strip element having a pair of opposite ends, said strip element being formed from a bibulous carrier material having a porous structure through which an aqueous dispersion system is capable of diffusing by capillary action, and (2) a capture component localized at a detection zone in the base element, said capture component comprising a capturing species capable of specifically binding to a capturable species, said detection zone being spaced from at least one of the ends of the strip element;

a first bath of dry, reconstitutable, water-dispersible first particles comprising a first coupling product of a first immunoreactive substance and a detectable label; and a second batch of dry, reconstitutable, water-dispersible second particles comprising a second coupling product of a second immunoreactive substance and said capturable species, the first and second particles of said first and second batches thereof being dispersible upon coming into contact with said aqueous sample to thereby form an aqueous dispersion system which contains said sample and dispersed first and second particles, said first and second immunoreactive substances being the same or different and being capable of specifically binding either competitively or non-competitively to sad analyte or to one another as a function of the presence or quantity of said analyte in said aqueous dispersion system to thereby form a dispersible composite reaction product comprising both first and second particles, said bibulous carrier material being such that the aqueous dispersion system will diffuse along the strip element and through the bibulous material so as to bring the composite reaction product into contact with the capture component localized at said detection zone to thereby immobilize and concentrate the composite reaction product at the detection zone so that the detection zone may then be evaluated for the presence of the detectable label as an indicator of the presence or quantity of the immunoreactive analyte in the aqueous sample.

31. The kit as set forth in claim 30, wherein said first and second particles are contained in the bibulous carrier material.

32. The kit as set forth in claim 31, wherein said first and second particles are contained in one or more contact zones in said bibulous material.

33. The kit as set forth in claim 32, wherein said first batch of particles is contained in a first contact zone in said bibulous material and said second batch of particles is contained in a second contact zone in said bibulous material.

34. The kit as set forth in claim 33, wherein said first and second contact zones are spaced apart longitudinally on or in said strip element.

35. The kit as set forth in claim 33, wherein said first and second contact zones are disposed between said one end of the strip element and said detection zone in longitudinally spaced relationship relative to the detection zone.

36. The kit as set forth in claim 34, wherein said first and second contact zones are disposed between said one end of the strip element and said detection zone in longitudinally spaced relationship relative to the detection zone.

37. The kit as set forth in claim 36, wherein said detectable label comprises a metal-containing third particle.

38. The kit as set forth in claim 37, wherein said first coupling product is prepared by coupling the first immunoreactive substance directly to the metal-containing third particle.

39. The kit as set forth in claim 37, wherein said metal containing third particles are metal sol particles.

40. The kit as set forth in claim 39, wherein said metal sol particles have a particle size in the range of from about 25 to about 1000 Angstroms.

41. The kit as set forth in claim 39, wherein said particles are gold sol particles.

42. The kit as set forth in claim 36, wherein one of said capturable and capturing species comprises biotin and other species comprises avidin.

43. The kit as set forth in claim 42, wherein said capturable species comprises biotin and said capturing species comprises avidin.

44. The kit as set forth in claim 36, wherein said capture component comprises a third coupling product of a fourth particle and said capturing species, said fourth particle being deposited and thus immobilized in the pores of said bibulous carrier material at said detection zone.

45. The kit as set forth in claim 44, wherein said capturable species comprises biotin and said capturing species comprises avidin.

46. The kit as set forth in claim 36, wherein said first and second immunoreactive substances each specifically binds a respective different site of the analyte to form a sandwich.

47. The kit as set forth in claim 46, wherein said first and second immunoreactive substances are each antibodies and the analyte is an antigen which is specifically bound by both antibodies.

48. The kit as set forth in claim 36, wherein said first and second immunoreactive substances specifically bind each other.

49. The kit as set forth in claim 48, wherein one of said immunoreactive substances is an antibody and the other is an antigen which is specifically bound by said antibody.

50. The kit as set forth in claim 48, wherein the first immunoreactive substance is an antibody and the second immunoreactive substance is an antigen which is specifically bound by said antibody.

51. The kit as set forth in claim 30, wherein is included a wick member disposed in intimate contact with said element at said one end thereof.

52. The kit as set forth in claim 36, wherein is included a wick member disposed in intimate contact with said element at said one end thereof.

* * * * *

UNITED STATES PATENT AND TRADEMARK OFFICE
CERTIFICATE OF CORRECTION

PATENT NO. : 5,141,850

DATED : August 25, 1992

INVENTOR(S) : Francis X. Cole, Eric C. Sigillo, Paul C. MacDonnell and Nancy J. Cicia It is certified that error appears in the above-identified patent and that said Letters Patent is hereby corrected as shown below:

Column 1, line 43, "ar" should be --are--;

line 58, "n" should be --no--.

Column 5, line 32, "ar" should be --are--.

Column 6, line 67, delete "used".

Column 7, line 47, delete "$OD_{533rm}$" and substitute --$OD_{533nm}$--;

line 55, delete "$OD_{533rm}$" and substitute --$OD_{533nm}$--.

Signed and Sealed this

Twenty-eighth Day of December, 1993

Attest:

BRUCE LEHMAN

Attesting Officer

Commissioner of Patents and Trademarks